United States Patent
Miwa (10) Patent No.: US 8,092,019 B2
(45) Date of Patent: Jan. 10, 2012

(54) NON-CONTACT ULTRASONIC TONOMETER

(75) Inventor: Tetsuyuki Miwa, Nukata-gun (JP)

(73) Assignee: Nidek Co., Ltd., Gamagori-shi (JP)

( * ) Notice: Subject to any disclaimer, the term of this patent is extended or adjusted under 35 U.S.C. 154(b) by 288 days.

(21) Appl. No.: 12/385,914

(22) Filed: Apr. 23, 2009

(65) Prior Publication Data

US 2009/0275820 A1 Nov. 5, 2009

(30) Foreign Application Priority Data

May 3, 2008 (JP) ................................. 2008-120795
Mar. 31, 2009 (JP) ................................. 2009-087600

(51) Int. Cl.
*A61B 3/10* (2006.01)
*A61B 3/14* (2006.01)
*A61B 3/16* (2006.01)

(52) U.S. Cl. ......... 351/205; 351/208; 600/399; 600/402

(58) Field of Classification Search .................. 351/208; 600/398–402
See application file for complete search history.

(56) References Cited

U.S. PATENT DOCUMENTS

| | | | |
|---|---|---|---|
| 3,948,248 A | 4/1976 | Zuckerman et al. | |
| 5,092,334 A | 3/1992 | Nishio et al. | |
| 5,636,635 A | 6/1997 | Massie et al. | |
| 5,865,742 A * | 2/1999 | Massie | 600/405 |
| 6,030,343 A * | 2/2000 | Chechersky et al. | 600/399 |
| 6,082,860 A * | 7/2000 | Takagi | 351/208 |
| 6,409,343 B1 * | 6/2002 | Uchida | 351/208 |
| 6,537,215 B2 * | 3/2003 | Miwa | 600/405 |
| 6,854,331 B2 | 2/2005 | Omata | |
| 7,434,932 B2 | 10/2008 | Hanebuchi | |
| 2003/0078486 A1 * | 4/2003 | Klein et al. | 600/398 |
| 2008/0297722 A1 * | 12/2008 | Honda | 351/208 |

FOREIGN PATENT DOCUMENTS

| | | |
|---|---|---|
| AU | 758525 B2 | 2/2002 |
| JP | A-63-197433 | 8/1988 |
| JP | A-2002-272743 | 9/2002 |
| JP | A-2004-267299 | 9/2004 |
| JP | A-2007-37984 | 2/2007 |
| WO | WO 03/030712 A2 | 4/2003 |

OTHER PUBLICATIONS

Jinde, Masayuki et al., "Development of a new non-contact intraocular pressure measurement system using a phase shift method", Conference of Institute of Electrical Engineers, Sensors and Micromachines Division, 2007, Doc. pp. 93-96 (w/English-language translation of excerpt).

* cited by examiner

*Primary Examiner* — Jordan Schwartz
(74) *Attorney, Agent, or Firm* — Oliff & Berridge, PLC (57) ABSTRACT

A non-contact ultrasonic tonometer for measuring intraocular pressure of an examinee's eye in non-contact manner by use of an ultrasonic wave comprises: a probe including a vibrator for making the ultrasonic wave incident on the eye and a sensor for detecting the ultrasonic wave reflected from the eye; a detection unit which detects an alignment state of the probe with respect to the eye; a determination unit which determines whether the alignment state is proper or not based on a detection result of the detection unit; a trigger signal generation unit which generates a trigger signal to start measurement based on a determination result of the determination unit; and a control unit which controls the probe to emit the ultrasonic wave based on generation of the trigger signal.

9 Claims, 8 Drawing Sheets

NON-CONTACT ULTRASONIC TONOMETER

TECHNICAL FIELD

The non-contact ultrasonic tonometer for measuring intraocular pressure of an examinee's eye in non-contact manner by ultrasound.

BACKGROUND ART

There is proposed a contact intraocular pressure examination apparatus for measuring intraocular pressure by pressing a distal end of a probe pen against an eye, the probe pen holding a probe device including a vibrator for introducing vibration into the eye and a vibration detecting sensor for detecting the vibration reflected by the eye (see Patent Literature 1: JP2004-267299A).

Also proposed is a non-contact intraocular pressure measurement system for measuring intraocular pressure by making an ultrasonic wave enter in an eye (actually, an eyeball model) and detecting the ultrasonic wave reflected from the eye by use of a sensor (see Non-patent Literature 1: "Development of a new non-contact intraocular pressure measurement system using a phase shift method", Masayuki JINDE and other three persons, Conference of Institute of Electrical Engineers, Sensors and Micromachines Division, Document p. 93-96, 2007). This system is arranged to measure a phase shift of a reflected wave with respect to a transmission wave as a frequency change, and determine a correlation between an amount of the frequency change and hardness of the eye model.

In the case of the apparatus configuration of Patent Literature 1, however, the probe pen is brought into contact with the eye to measure intraocular pressure and thus a large burden would be given to the eye. The apparatus configuration of Non-patent Literature 1 is merely intended to measure the eyeball model, which is insufficient to measure human eyes. In the case of measuring human eyes, which exhibit involuntary eye movement and visual line movement, the ultrasonic wave characteristics (e.g., frequency and phase) detected by the sensor are likely to vary due to misalignment of the apparatus with the eye, leading to variations in measurement results.

SUMMARY OF INVENTION

Technical Problem

The present invention has a purpose to provide a non-contact ultrasonic tonometer capable of easily making alignment of the tonometer with respect to an examinee's eye.

Solution to Problem

To achieve the above purpose, the present invention provides a non-contact ultrasonic tonometer for measuring intraocular pressure of an examinee's eye in non-contact manner by use of an ultrasonic wave, the tonometer comprising: a probe including a vibrator for making the ultrasonic wave incident on the eye and a sensor for detecting the ultrasonic wave reflected from the eye; a detection unit which detects an alignment state of the probe with respect to the eye; a determination unit which determines whether the alignment state is proper or not based on a detection result of the detection unit; a trigger signal generation unit which generates a trigger signal to start measurement based on a determination result of the determination unit; and a control unit which controls the probe to emit the ultrasonic wave based on generation of the trigger signal.

DESCRIPTION OF EMBODIMENTS

Figure 1:
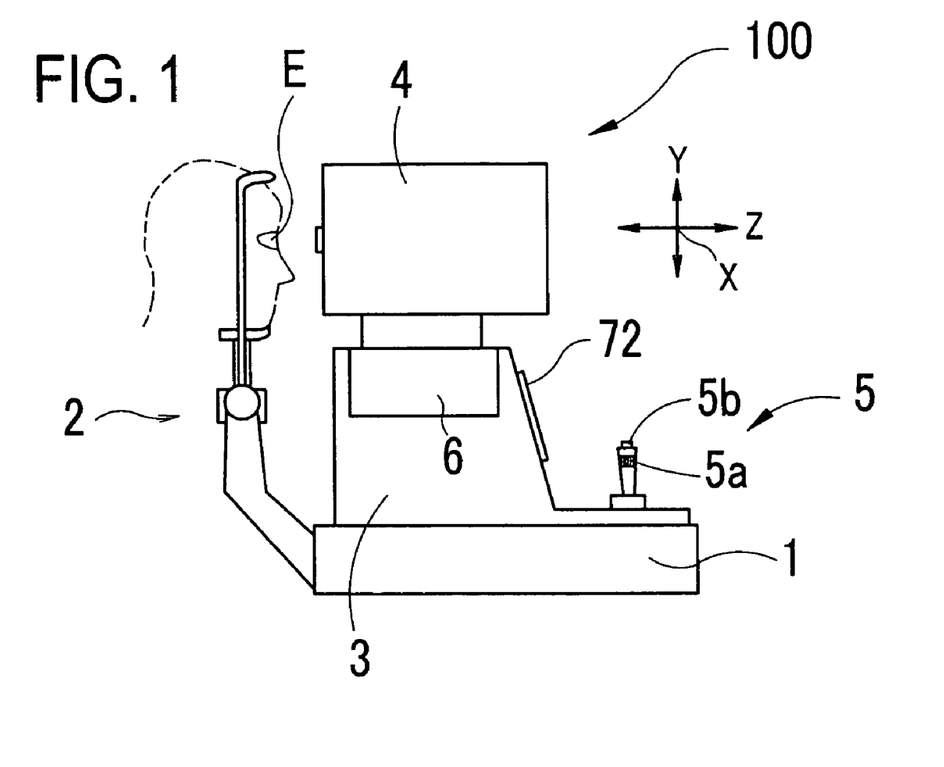
FIG. 1 is a perspective external view of a non-contact ultrasonic tonometer of a preferred embodiment of the present invention.

A preferred embodiment of the present invention will be described below with reference to accompanying drawings. FIG. 1 is a perspective external view of a non-contact ultrasonic tonometer 100 of this embodiment.

The tonometer 100 is a so-called stationary apparatus including a base 1, a head support unit 2 attached to the base 1, a movable unit 3 movably placed on the base 1, and a measurement part 4 that is movably provided on the movable base 3 and contains a measurement system and optical systems mentioned later. The measurement part 4 is moved in a right-and-left direction (an X-direction), an up-and-down direction (a Y-direction), and a back-and-force direction (a working distance direction; a Z-direction) relative to an examinee's eye E by a movement part 6 provided in the movable unit 3. The movable unit 3 is moved in the X- and Z-directions on the base 1 by inclining operation of a joystick 5. The measurement part 4 is moved in the Y-direction by the movement part 6 by a rotating operation of a knob 5a. The joystick 5 is provided, at its top, with a measurement start switch 5b. On the movable base 3, a monitor 72 is provided.

Figure 2:
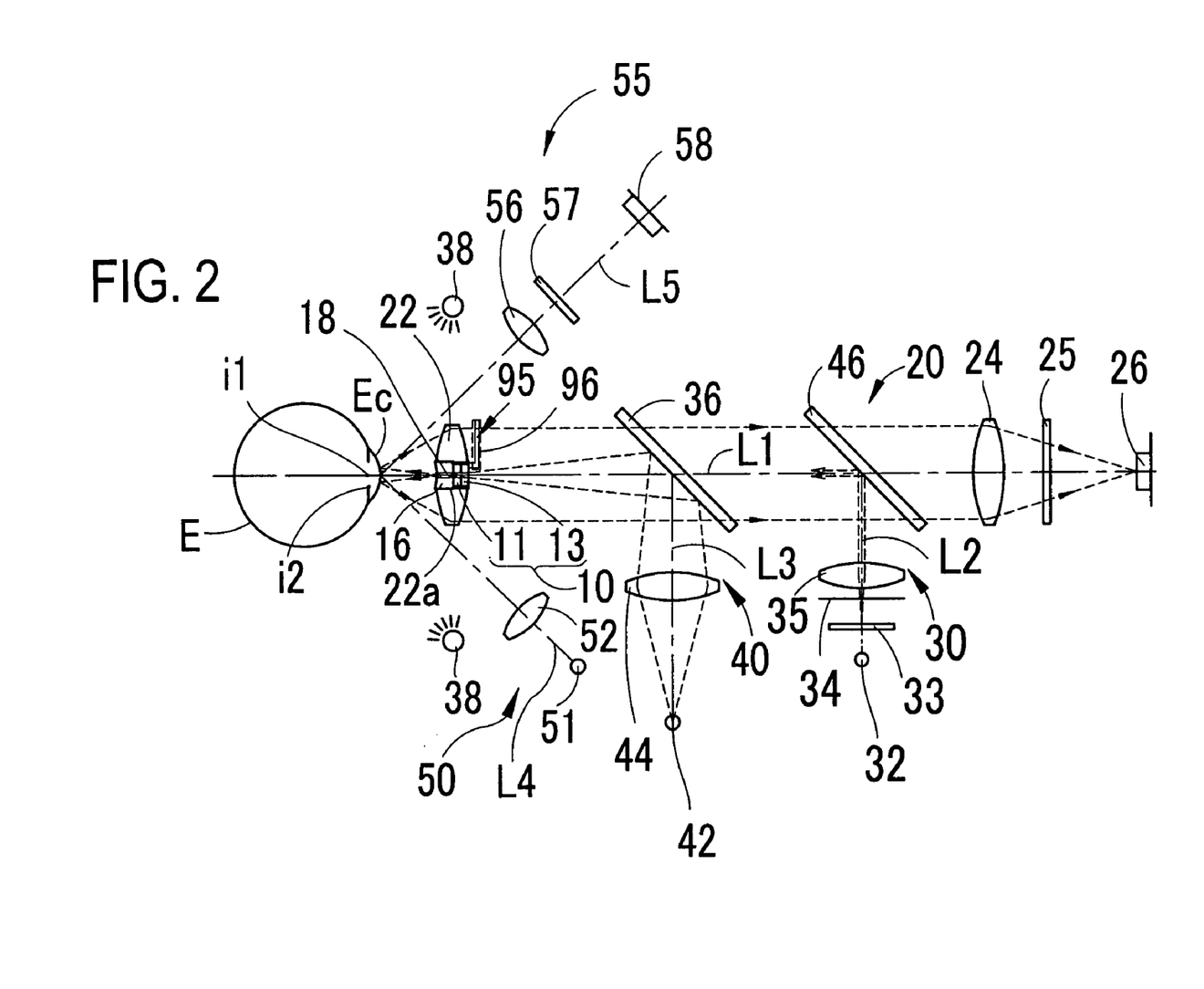
FIG. 2 is a perspective configuration view of a measurement system and an optical system of the tonometer.
Figure 3:
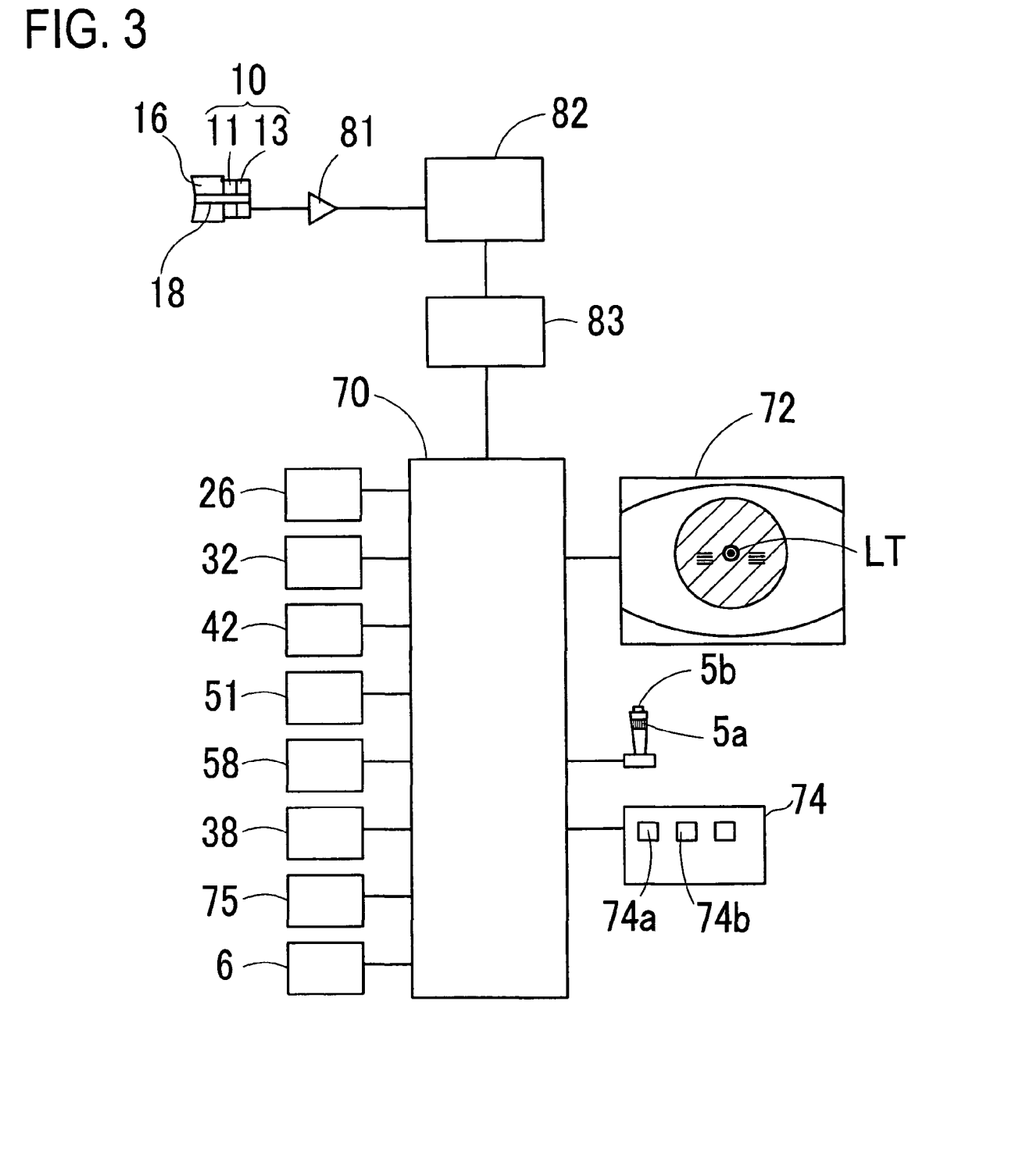
FIG. 3 is a perspective configuration view (partly a block diagram) of a control system of the tonometer.

FIG. 2 is a perspective configuration view of the measurement system and optical systems of the tonometer 100, showing a case where a probe is placed in an optical path of an observation optical system. FIG. 3 is a perspective configuration view (partly a block diagram) of a control system of the tonometer 100.

A probe (a transducer) 10 placed in front of the examinee's eye E has a vibrator (an ultrasonic wave transmitting section) 11 for making an ultrasonic wave (an incident wave, a transmission wave) incident on the eye E and a sensor (an ultrasonic wave receiving section) 13 for detecting an ultrasonic wave (a reflected wave, a received wave) reflected by the eye E. The probe 10 is constituted of for example two piezoelectric elements arranged one on another. One of the piezoelectric elements is used as the vibrator 11 and the other is used as the sensor 13. In this embodiment, a pulse wave is used as the ultrasonic wave made incident on the eye E but a continuous wave may be used instead.

On the side of the probe 10 closer to the eye E, an acoustic lens 16 is placed to converge the ultrasonic wave from the vibrator 11. This lens 16 comes into focus on the eye E when the probe 10 is placed in proper alignment with the eye E.

The probe 10 is connected sequentially to an amplifier 81, a frequency component analysis section 82, a frequency phase difference specifying section 83, and an arithmetic and control section 70. An electric signal corresponding to an incident wave and a reflected wave is amplified to an appropriate signal level by the amplifier 81 and subjected to frequency component analysis by the analysis section 82 to obtain a spectral distribution of the phase difference with respect to the frequency. The specifying section 83 compares the spectral distribution of the incident wave and the spectral distribution of the reflected wave to specify a phase difference $\theta x$ which is a difference in phase between the incident wave and the reflected wave at respective frequencies fx. The phase difference $\theta x$ at the frequency fx will vary according to intraocular pressure (strictly speaking, changes in hardness of a cornea of the examinee's eye E resulting from changes in the intraocular pressure). Accordingly, the arithmetic and control section 70 detects the phase difference $\theta x$ based on an output signal of the specifying section 83 and obtains the intraocular pressure of the eye E based on the detection result. This method is referred to U.S. Pat. No. 6,854,331 (JP2002-272743A).

The probe 10 and the lens 16 are formed, at respective centers, with an aperture 18 (e.g., a circular hole having a diameter of about 1 mm) through which fixation target projecting light (hereinafter, referred to as "fixation target light") from a light source 32 and alignment mark projecting light (hereinafter, referred to as "alignment mark light") from a light source 42 are allowed to pass.

The vibrator 11 and the sensor 13 are electrically connected to a circuit system (the amplifier 81, the analysis section 82, the specifying section 83, the arithmetic and control section 70, and others) disposed out of an optical path of the observation optical system 20 (hereinafter, referred to as an "observation optical path") with a wiring cable 95. This cable 95 is covered with a cover 96 applied with a coating for absorbing reflected light (e.g., infrared light) from an anterior segment of the eye E. This makes it possible to prevent the reflected light by the anterior segment from diffusing on the surface of the cable 95 to be detected as noise light by a two-dimensional image pickup device 26.

Provided as the optical systems of the tonometer 100 are the observation optical system 20 for observing the anterior segment of the eye E, a fixation target projection optical system 30 for causing the eye E to hold fixation, a first alignment mark projection optical system 40 for projecting an alignment mark in the X- and Y-directions to the eye E, a second alignment mark projection optical system 50 for projecting an alignment mark in the Z-direction to the eye E, and an alignment mark detection optical system 55 for detecting the Z-direction alignment mark projected onto the eye E.

The observation optical system 20, having the optical path in which the probe 10 is placed, forms an image of the anterior segment through a region surrounding the probe 10. Specifically, the observation optical system 20 includes, an objective lens 22, an imaging lens 24, a filter 25, and the image pickup device 26 and provides an optical axis (hereinafter, an "observation optical axis") L1 in which the probe 10 is placed. Thus, when the observation optical axis L1 is aligned to a predetermined portion (for example, a corneal center or a pupil center of the eye E), the probe 10 is placed in front of the eye E. Furthermore, in the configuration of FIG. 2, the probe 10 is arranged so that the central axis (an extension of the central axis) of the probe 10 is coaxial with the observation optical axis L1. Accordingly, when the observation optical axis L1 is aligned with the predetermined portion of the eye E, the central axis of the probe 10 comes to coincide with the predetermined portion of the eye E and therefore an ultrasonic wave reflected by the eye E can be efficiently detected.

Light sources 38 which emit infrared light to illuminate the anterior segment of the eye E are disposed diagonally to the front of the eye E. The filter 25 has a property of transmitting the light from each light source 38 and the light from the light source 42 and blocking light from a the light source 51.

The light from each light source 38 is projected onto the anterior segment of the eye E and then the light reflected by the anterior segment travels toward the lens 22. The light reaching the surrounding region of the probe 10 passes through the lens 22, further passes a half mirror 36 and a dichroic mirror 46, and forms an image on the image pickup device 26 by the lens 24. Specifically, the anterior segment image by the light source 38 is formed on the image pickup device 26 through the surrounding region of the probe 10. The dichroic mirror 46 has a property of transmitting the light from each light source 38 and the light from the light source 42 and reflecting the light from the light source 32.

A signal output from the image pickup device 26 is input to the arithmetic and control section 70. The picked-up anterior segment image is displayed on the monitor 72. In the configuration of FIG. 2, an imaging optical system (a lens system constituted of a plurality of lenses) including the lenses 22 and 24 is used as a light delivery member for delivering the anterior segment image to the image pickup device 26. Alternatively, a single lens may be used to deliver the anterior segment image to the image pickup device 26.

Figure 5:
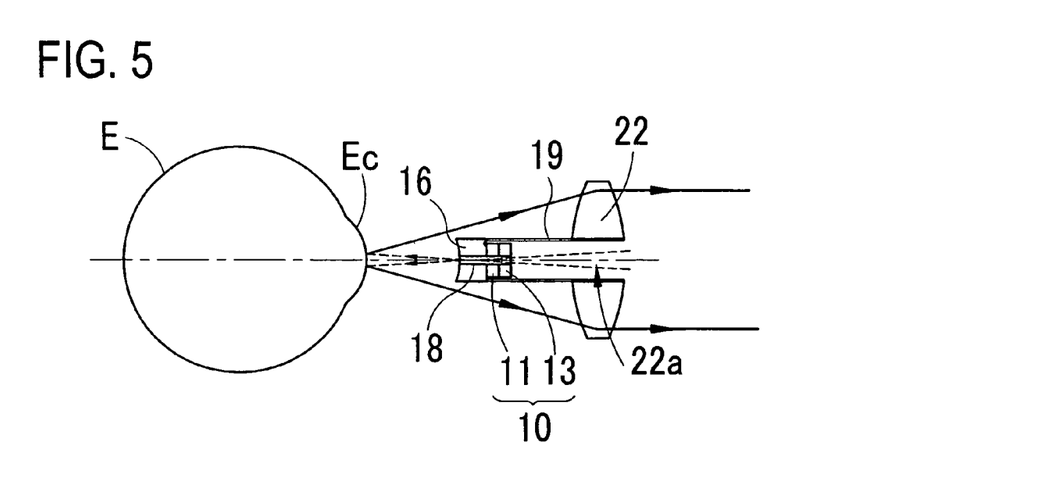
FIG. 5 is a view showing a case where an objective lens is placed behind a probe.

For a positional relationship between the probe 10 and the lens 22 in the direction of the observation optical axis L1 (the Z-direction), the lens 22 is placed behind the probe 10 (closer to the image pickup device 26) or in the same position as the probe 10 and hence wider space can be provided between the eye E and a housing of the apparatus (see FIGS. 2 and 5). In this case, the reflected light from the anterior segment may be interrupted by the probe 10 and the lens 16. In order to allow clear observation of the anterior segment image, the probe 10 and the lens 22 are preferably placed close to each other on the observation optical axis L1 and more preferably placed in substantially the same position on the observation optical axis L1.

FIG. 2 shows one example of the configuration in which the probe 10 and the lens 22 are placed in the same position. That is, the lens 22 is formed, in almost the center thereof, with an aperture 22*a* in which the probe 10 is inserted. In this aperture 22*a*, the probe 10 and the lens 16 are set.

FIG. 5 shows one example of the configuration in which the lens 22 is placed behind the probe 10. Specifically, the lens 22 is formed, in almost the center thereof, with the aperture 22*a* in which a support member 19 is inserted. The probe 10 and the lens 16 are set in a forward position in the support member 19 inserted in the aperture 22*a*.

Alternatively, the lens 22 may be placed before the probe 10. In this case, the lens 22 is preferably formed with an aperture in a position corresponding to an ultrasonic wave propagation path in order to prevent the lens 22 from reflecting and attenuating the ultrasonic wave from the probe 10. Thus, the incident wave from the vibrator 11 is allowed to enter the eye E through the aperture and the reflected wave from the eye E is detected by the sensor 13 through the aperture.

The fixation target projection optical system 30 includes at least a fixation target projection light source to project a fixation target onto the eye E to cause the eye E to view the fixation target. Specifically, the projection optical system 30 includes the light source 32, a fixation target 33, a diaphragm 34, a projection lens 35, and the dichroic mirror 46 to project the fixation target onto the eye E through the aperture 18. An optical axis L2 of the projection optical system 30 is made coaxial with the observation optical axis L1 by the dichroic mirror 46 located in the observation optical path.

Light of the fixation target 33 illuminated by visible light from the light source 32 is reduced in light diameter by the diaphragm 34, passes through the lens 35, is reflected by the dichroic mirror 46, passes through the half mirror 36, and then is projected onto the fundus of the eye E through the aperture 18. Thus, the eye E holds fixation.

The first alignment mark projection optical system 40 includes at least an alignment mark projecting light source to project an alignment mark in the X- and Y-directions onto the eye E from front. Specifically, the projection optical system 40 includes the light source 42, a projection lens 44, and the half mirror 36 to project the alignment marks (the alignment mark light) onto the eye E through the aperture 18. An optical axis L3 of the projection optical system 40 is made coaxial with the observation optical axis L1 by the half mirror 36 located in the observation optical path.

Infrared light from the light source 42 passes through the lens 44, is reflected by the half mirror 36, and then is projected onto the cornea of the eye E through the aperture 18. Light mirror-reflected by the cornea forms an image (an alignment mark image) i1 which is a virtual image (a corneal reflection image) of the light source 42.

The light of the mark image i1 travels toward the lens 22. The light reaching the surrounding region of the probe 10 passes through the lens 22, the half mirror 36, and the dichroic mirror 46, and forms an image on the image pickup device 26 by the lens 24. In other word, the mark image i1 by the light source 42 is formed on the image pickup device 26 through the surrounding region of the probe 10. When the eye E moves in the X- and Y-directions, an image forming position of the mark image i1 also moves on the image pickup device 26. Based on a detection signal of the image pickup device 26, the arithmetic and control section 70 can detect an alignment state of the apparatus (the probe 10) in the X- and Y-directions with respect to the eye E.

In the case of projecting the alignment mark light through the aperture 18 formed in the probe 10 and the lens 16 and receiving the reflected light from the eye E through the surrounding region of the probe 10, part of the reflected light may be interrupted by the lens 16. To avoid such defect, as shown in FIG. 2, the projection optical system 40 is preferably configured as an optical system whereby the alignment mark light is converged once before reaching the eye E and then is projected as dispersion light onto the cornea.

The second alignment mark projection optical system 50 includes at least an alignment mark projecting light source to project an alignment mark in the Z-direction onto the eye E from an oblique direction. Specifically, the projection optical system 50 includes the light source 51 and a projection lens 52 to project the alignment mark (the alignment mark light) onto the eye E. An optical axis L4 of the projection optical system 50 intersects with the observation optical axis L1 at a predetermined angle.

Infrared light from the light source 51 passes through the lens 52, is substantially collimated, and then is projected onto the cornea of the eye E. The light mirror-reflected by the cornea forms an image (an alignment mark image) i2 which is a virtual image (a corneal reflection image) of the light source 51.

The alignment mark detection optical system 55 includes a photo-receiving lens 56, a filter 57, and a position sensitive device 58 (e.g., a line CCD) to detect the alignment mark image formed by the projection optical system 50. The filter 57 has a property of transmitting the light from the light source 51 and blocking the light from the light source 38 and the light from the light source 42. An optical axis L5 of the detection optical system 55 is symmetrical to the optical axis L4 of the projection optical system 50 with respect to the observation optical axis L1. The optical axis L5 intersects with the optical axis L4 at a point on the optical axis L1.

The mark image i2 by the light source 51 is formed on the position sensitive device 58 by the lens 56. When the eye E moves in the Z-direction, an image forming position of the mark image i2 moves on the position sensitive device 58. Based on a detection signal of the position sensitive device 58, the arithmetic and control section 70 can detect an alignment state of the apparatus (the probe 10) in the Z-direction with respect to the eye.

The arithmetic and control section 70 is coupled to the knob 5a, the switch 5b, the movement part 6, the monitor 72, the specifying section 83, the light sources 32, 38, 42, and 51, the image pickup device 26, the position sensitive device 58, an operation section (an input section) 74 provided with various switches, a memory 75 serving as a storage section, and others. The arithmetic and control section 70 performs control of the entire apparatus, calculation of measured values, and so on.

The memory 75 stores a table showing a correlation between the phase difference θx at the frequency fx and an intraocular pressure value. The arithmetic and control section 70 retrieves an intraocular pressure value corresponding to the detected phase difference θx from the memory 75 based on the output signal of the specifying section 83 and displays the retrieved intraocular pressure value on the monitor 72.

The correlation between the phase difference θx and the intraocular pressure value can be set by experimentally determining in advance a correlation between phase differences θx obtained by the present apparatus and intraocular pressure values measured by a Goldmann tonometer. The memory 75 stores a program for measuring intraocular pressure by use of the probe 10, a program for controlling the entire apparatus, and so on.

On the operation part 74, there are arranged a selection switch 74a for selecting either an automatic alignment mode of automatically aligning the measurement part 4 with respect to the eye E or a manual alignment mode of manually aligning the measurement part 4 with respect to the eye E, a selection switch 74b for selecting either an automatic shot mode of automatically generating a trigger signal to start measurement upon completion of alignment or a manual shot mode of generating a trigger signal to start measurement based on an operation signal of the switch 5b, and others. When the automatic shot mode is selected, the arithmetic and control section 70 determines whether the alignment state is proper or not based on each detection signal of the image pickup device 26 and the position sensitive device 58. Based on the determination result, the arithmetic and control section 70 generates a measurement-start trigger signal and, based on the generation of the trigger signal, causes the probe 10 to emit an ultrasonic wave to the eye E.

Figure 4A:
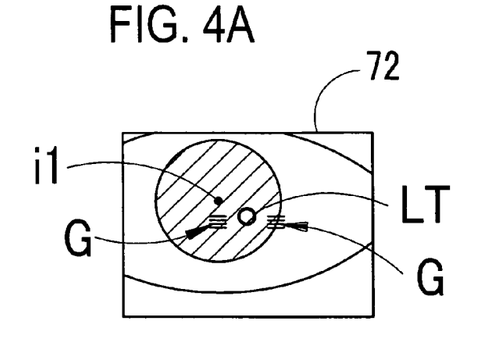
FIGS. 4A and 4B are views showing examples of an observation screen displayed on a monitor.
Figure 4B:
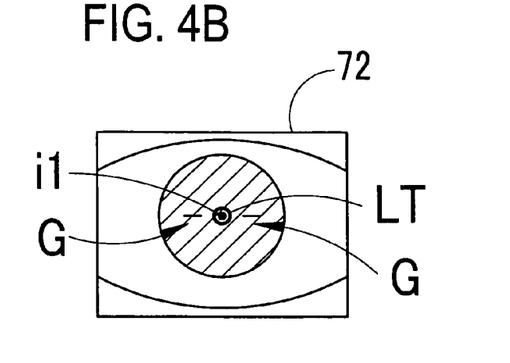

Operations of the apparatus having the above configuration are explained below. Firstly, the face (head) of an examinee is fixed on the head support unit 2. An examiner makes alignment of the apparatus with the examinee's eye E by manipulating the joystick 5 while viewing the monitor 72. At that time, the arithmetic and control section 70 displays the anterior segment image picked up by the image pickup device 26 and a reticle LT and an indicator G for alignment on the monitor 72 as shown in FIGS. 4A and 4B.

When the mark image i1 starts to appear on the monitor 72 (when the image pickup device 26 starts to detect the mark image i1), the automatic alignment in the X- and Y-directions is enabled. Furthermore, when the position sensitive device 58 starts to detect the mark image i2, the automatic alignment in the Z-direction is enabled. The arithmetic and control section 70 controls display of the indicator G based on information about the alignment state in the Z-direction obtained from the detection signal of the position sensitive device 58.

The case of selecting the automatic alignment mode and the automatic shot mode is explained below. The arithmetic and control section 70 obtains misalignment amounts of the apparatus in the X-, Y-, and Z-directions relative to the eye E located in a proper position, and controls driving of the movement part 6 to bring each misalignment amount into a predetermined permissible range. When each misalignment amount falls within the permissible range, the arithmetic and control section 70 stops the driving of the movement part 6 and automatically generates the measurement-start trigger signal to start intraocular pressure measurement.

The case of selecting the manual alignment mode and the manual shot mode is explained below. In this case, the examiner manipulates the joystick 5 (the knob 5a) so that the mark image i1 displayed on the monitor 72 enters in the reticle LT and the indicator G appears in the form representing alignment completion (see FIG. 4B). When the alignment is completed in each direction and the switch 5b is pressed by the examiner, the arithmetic and control section 70 generates the measurement-start trigger signal to start the intraocular pressure measurement.

Upon generation of the measurement-start trigger signal, the arithmetic and control section 70 causes the vibrator 11 to emit the ultrasonic wave to the eye E and detects the ultrasonic wave reflected from the eye E by the sensor 13. The arithmetic and control section 70 calculates an intraocular pressure value of the eye E based on the output signal of the specifying section 83 and displays a result thereof on the monitor 82.

With the above configuration, the alignment between the eye E and the probe 10 can be easily performed.

In the above explanation, the fixation target light is projected onto the eye E through the aperture 18 formed in the center of the probe 10. It is not limited thereto but may be arranged to project the fixation target light through the surrounding region of the probe 10 in the lens 22. A conceivable configuration in this case is, for instance, to use a diaphragm having an annular aperture centered on the optical axis L2 instead of the diaphragm 34 having a spot aperture on the optical axis L2.

In the above embodiment, the alignment mark light is projected onto the eye E through the aperture 18 formed in the center of the probe 10. It is not limited thereto but may be arranged to project the alignment mark light through the surrounding region of the probe 10 in the lens 22, and allow the image pickup device 26 to detect the reflected light passing through the surrounding region of the probe 10 in the lens 22. A conceivable configuration in this case is, for instance, to use an annular light source instead of the spot light source 42.

Figure 6:
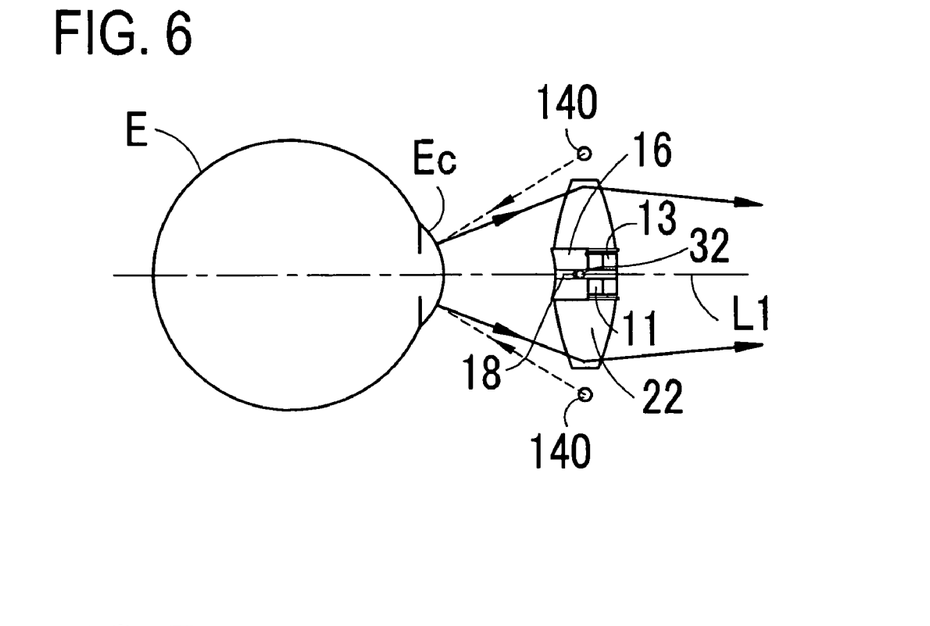
FIG. 6 is a view showing a modified example of a fixation target projection optical system and a first alignment mark projection optical system.

FIG. 6 is a view showing a modified example of the fixation target projection optical system and the first alignment mark projection optical system. In this case, the light source 32 (e.g., an LED) is placed in the center of the probe 10.

A first alignment mark projection optical system 140 for projecting alignment mark light at a predetermined angle to the observation optical axis L1 is placed outside the lens 22. Reflected light thereof is allowed to pass through the surrounding region of the probe 10 in the lens 22. In this case, the angle of the optical axis of the projection optical system 140 to the observation optical axis L1 is determined to prevent part of the reflected light from becoming interrupted by the lens 16.

In the case where the light source 32 is placed in the center of the probe 10 as shown in FIG. 6, a light source that emits visible light and infrared light may be used as the light source 32 to serve both as the fixation target projecting light source and the alignment mark projecting light source.

Figure 7:
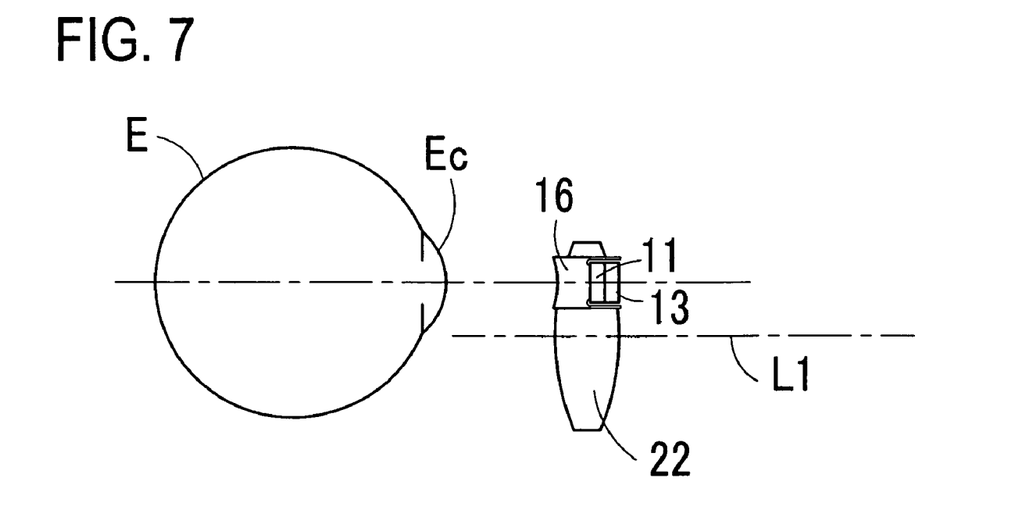
FIG. 7 is a view showing a case where the probe is displaced in a direction perpendicular to an optical axis of an observation optical system.

In the above explanation, the probe 10 is placed on the observation optical axis L1 but not limited thereto. The probe 10 may be displaced from the observation optical axis L1 in a direction (the X- and Y-directions) perpendicular to the optical axis L1 as shown in FIG. 7. In this case, a detection position of the mark image i1 on the image pickup device 26 when the central axis (the extension of the central axis) of the probe 10 comes into alignment with the predetermined portion (e.g., the corneal center or the pupil center) of the eye E is set as an alignment reference position, and a display position of the reticle LT, an alignment completion position, and others are set.

Figure 8:
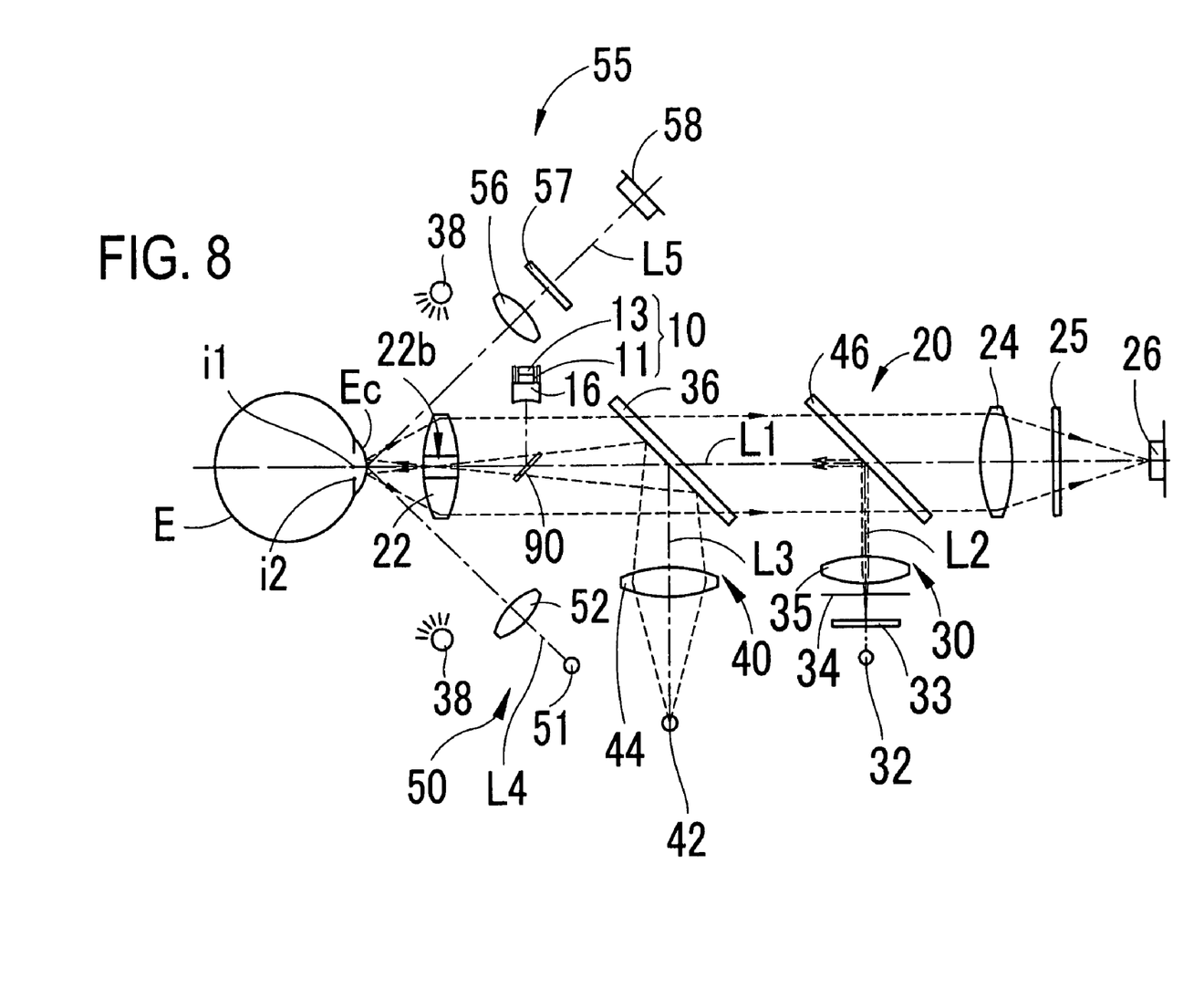
FIG. 8 is a view showing a case where the probe is placed out of an optical path of the observation optical system.

FIG. 8 is a schematic configuration view of the measurement system and the optical system of the tonometer 100, showing the case where the probe is placed out of the optical path of the observation optical system.

An ultrasonic wave reflecting member (an acoustic mirror) 90 reflects an incident wave from the vibrator 11 toward the eye E while reflecting a reflected wave from the eye E toward the sensor 13. The observation optical system 20 is arranged so that the probe 10 is placed out of the optical path thereof and the observation optical axis L1 is positioned on an ultrasonic wave propagation path between the reflecting member 90 and the eye E. The lens 22 is formed with an aperture 22b through which an ultrasonic wave from the probe 10 is allowed to pass. The incident wave from the vibrator 11 is reflected by the reflecting member 90 to enter the eye E after passing through the aperture 22b. The reflected wave from the eye E passes through the aperture 22b, is reflected by the reflecting member 90, and then is detected by the sensor 13.

In the case where the lens 22 is placed between the reflecting member 90 and the eye E, the lens 22 formed with the aperture 22b in a portion corresponding to the ultrasonic wave propagation path can avoid attenuation of the ultrasonic wave which is likely to be caused in passing through the lens 22. In this case, the reflecting member 90 applied with a coating having a property of blocking the reflection light from the anterior segment by the light source 38 may be used to prevent the anterior segment reflection light from entering the image pickup device 26 through the aperture 22b, thereby preventing resultant noise light.

As the reflecting member 90, a member having a property of reflecting the ultrasonic wave and transmitting light (for example, a transparent and colorless, hard plastic plate) may be used. This can prevent the fixation target light and the alignment mark light from becoming interrupted even when the reflecting member 90 is placed in each optical path of the projection optical system 30 and the projection optical system 40. In the case of using the reflecting member 90 having a light transmission property, taking into consideration that the optical length is changed by passage of light through the reflecting member 90, a member having the area almost equal to an optical path splitting member such as the half mirror 36 and the dichroic mirror 46 may be used.

The present invention is not limited to the above configuration and may be arranged such that the reflecting member 90 is partly provided with an aperture through which the fixation target light and the alignment mark light are allowed to pass to be projected onto the eye E. The above configuration shows the case in which the reflecting member 90 is placed in a common optical path of the projection optical systems 30 and 40. The above configuration can be applied to the case where the reflecting member 90 is placed in the optical path of at least one of the projection optical systems 30 and 40.

The configuration in which the probe 10 is placed out of the observation optical path is not limited to one shown in FIG. 8 and may be arranged so that the reflecting member 90 is placed between the lens 22 and the eye E. In this case, the incident wave from the vibrator 11 is reflected by the reflecting member 90 to enter the eye E, while the reflected wave from the eye E is reflected by the reflecting member 90 and detected by the sensor 13.

Figure 9:
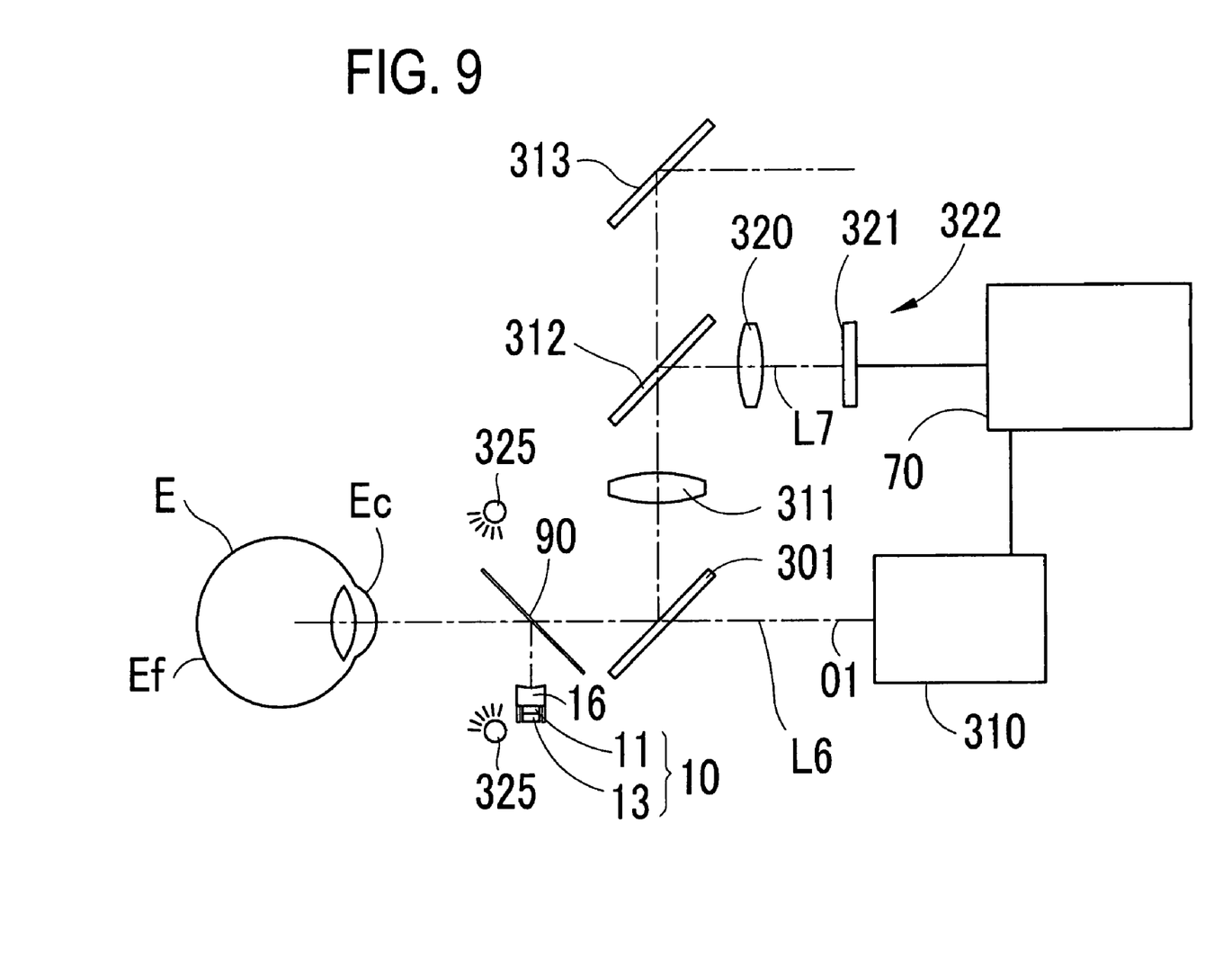
FIG. 9 is a view showing a case where the tonometer is provided with an eye refractive power measurement optical system.

The tonometer may be additionally provided with a measurement optical system for measuring eye characteristics different from the intraocular pressure. FIG. 9 is a view showing the case where an eye refractive power measurement optical system is added to the tonometer.

An eye refractive power measurement optical system 310 is arranged so that the probe 10 is placed out of an optical path of the measurement optical system 310 (a measurement optical path), and an optical axis L6 of the measurement optical system 310 (hereinafter, referred to as a "measurement optical axis") is located on the ultrasonic wave propagation path between the reflecting member 90 and the eye E. The reflecting member 90 is placed in front of the eye E. The incident wave from the vibrator 11 is reflected by the reflecting member 90 to enter the eye E and the reflected wave from the eye E is reflected by the reflecting member 90 and detected by the sensor 13. Thus, the intraocular pressure of the eye E is measured.

The measurement optical system 310 is placed on the transmission side of a dichroic mirror 301 located at the rear of the reflecting member 90. The measurement optical system 310 is an optical system for projecting measurement light to the fundus of the eye E and receiving reflected light from the fundus by a photo-receiving device. Based on an output signal of the photo-receiving device, the eye refractive power is measured. The measurement optical system 310 and a measurement principle of eye refractive power are well known and thus their details are omitted herein.

On the reflection side of the dichroic mirror 301, an objective lens 311, a dichroic mirror 312, and a total reflection mirror 313 are placed. On the reflection side of the mirror 313, a fixation target projection optical system not shown is arranged to cause the eye E to view the fixation target.

On the reflection side of the dichroic mirror 312, arranged is an observation optical system 322 including an imaging lens 320 and a two-dimensional image pickup device 321 placed in a substantially conjugate relationship with the vicinity of the anterior segment of the eye E. The image pickup device 321 picks up the anterior segment image formed by a light source 325 and a mark image formed by the alignment mark projection optical system not shown.

The measurement optical axis L6 and an optical axis L7 of the observation optical system 322 are made coaxial by the dichroic mirror 301. The dichroic mirror 301 has a property of transmitting light from a light source of the measurement optical system 310 and reflecting the light from the light source 325, light from a light source of the alignment mark projection optical system, and light from a light source of the fixation target projection optical system. The dichroic mirror 312 also has a property of transmitting the light from the light source of the fixation target projection optical system and reflecting the light from the light source 325 and the light from the light source of the alignment mark projection optical system. Used as the reflecting member 90 is a member having a property of reflecting an ultrasonic wave and transmitting light (e.g., a transparent and colorless, hard plastic plate). This member transmits the measurement light by the measurement optical system 310, the anterior segment reflected light by the light source 325, the fixation target light by the fixation target projection optical system, the alignment mark light by the alignment mark projection optical system, and others.

In the configuration of FIG. 9, the reflecting member 90 is placed in a common optical path of the measurement optical system 310, the observation optical system 322, and the fixation target projection optical system but it is not limited thereto. The configuration has only to reflect the ultrasonic wave from the probe 10 by the reflecting member 90 to enter the eye E from front. For instance, the reflecting member 90 may be placed between the dichroic mirror 301 and the lens 311.

Although the above explanation exemplifies the eye refractive power measurement optical system, the present invention is not limited thereto and may be applied to a measurement optical system for measuring eye characteristics different from intraocular pressure by receiving reflected light resulting from measurement light projected onto the eye E. For example, a non-contact type eye axial length measurement optical system (e.g., see U.S. Pat. No. 7,434,932 (JP2007-37984A), a corneal thickness measurement optical system (e.g., see JP63-197433(1988)A), and others may be adopted.

Furthermore, a mode of performing intraocular pressure measurement based on the measurement-start trigger signal may be selected as needed with a switch or the like between a normal measurement mode of performing one intraocular pressure measurement in response to one trigger signal and a continuous measurement mode of repeating intraocular pressure measurements several times in response to one trigger signal.

The case of selecting the continuous measurement mode is explained below. Upon generation of the measurement-start trigger signal, the arithmetic and control section 70 causes the probe 10 to continuously emit an ultrasonic wave pulse toward the eye E to obtain information on variations in intraocular pressure caused by pulsation of the eye E, and performs the arithmetic processing corresponding to each ultrasonic wave pulse continuously emitted.

Specifically, the ultrasonic wave pulse is continuously made incident on the eye E at predetermined time intervals (e.g., 0.1 seconds intervals) within a range (e.g., within 1.5 seconds) of a pulsation cycle of the eye E, and an intraocular pressure value corresponding to each ultrasonic wave pulse is calculated. In this way, many intraocular pressure values can be obtained within the range of the pulsation cycle and thus variations in intraocular pressure values in the pulsation cycle can be captured. In this case, based on each measured value obtained within the range of the pulsation cycle, it is possible to calculate a representative value (e.g., an average value of the measured values, a central value of the measured values) and calculate measured values at a peak, a bottom, and a middle of the pulsation.

In the above explanation, the ultrasonic wave pulse is emitted at the predetermined time intervals (e.g., 0.1 seconds intervals) but not limited thereto. The ultrasonic wave pulse may be emitted at a predetermined number of times previously set within the range of the pulsation cycle. The time intervals and number of emissions for continuously emitting the ultrasonic wave pulse may be made arbitrarily settable and a switch thereof may be provided in the operation part 74.

In the above explanation, the alignment state of the apparatus with respect to the eye E in the Z-direction is optically detected (a working distance is detected) but it may be detected by the probe 10 used for intraocular pressure measurement. In this case, the control of the probe 10 has to be switched between control for measuring the intraocular pressure and control for detecting the working distance. In the case of detecting the working distance with respect to the eye E by use of the probe 10, the arithmetic and control section 70 measures a measurement time T from emission of the incident wave from the vibrator 11 toward the eye E until the reflected wave from the eye E is detected by the sensor 13 and thereby detects the working distance of the probe 10 from the eye E. In other words, as the measurement time T from the emission of the ultrasonic wave from the vibrator 11 until the ultrasonic wave is detected by the sensor 13 is longer, the working distance is larger. As the measurement time T is shorter, the working distance is smaller. The arithmetic and control section 70 previously determines a reference measurement time Tk for which the working distance is proper with respect to the eye E and considers the alignment in the Z-direction to be completed when the measurement time T reaches the reference measurement time Tk.

In the case of the above configuration, for example, the arithmetic and control section 70 controls the probe 10 as a working distance sensor with respect to the eye E before completion of alignment and controls the probe 10 as an intraocular pressure measurement sensor with respect to the eye E after completion of alignment. This can facilitate the configuration for detecting the alignment state of the apparatus relative to the eye E in the Z-direction.

The above explanation is made to determine the intraocular pressure based on a difference in acoustic impedance resulting from the phase difference between an input phase and an output phase. The present invention is not limited thereto and may be applied to a configuration that can determine intraocular pressure by performing a comparison and arithmetic processing of the incident wave from the vibrator 11 and the reflected wave detected by the sensor 13. For instance, it may be arranged to determine intraocular pressure by performing a comparison and arithmetic processing of the frequency of the incident wave from the vibrator 11 and the frequency of the reflected wave detected by the sensor 13. Specifically, a phase shift circuit may be provided to shift the phase difference to zero by changing the frequency of an ultrasonic wave generated by the vibrator 11 when the phase difference occurs between the input waveform to the vibrator 11 and the output waveform from the sensor 13. The intraocular pressure is determined by detecting a frequency change amount when the phase difference is shifted to zero.

Figure 10:
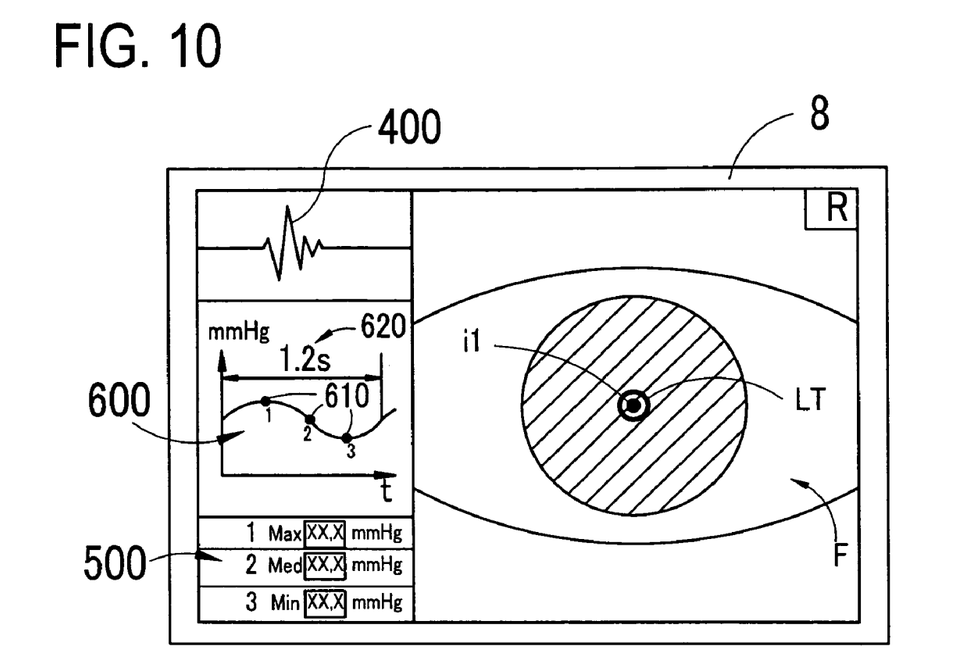
FIG. 10 is a view showing an example of a screen appearing on the monitor.

FIG. 10 is a view showing an example of a screen appearing on the monitor 72. The control section 70 simultaneously displays, on the monitor 72, an anterior segment image F picked up by the image pickup device 26, a waveform indication 400 showing a waveform of a reflected wave, an intraocular pressure value indication 500 showing a plurality of intraocular pressure values, and an intraocular pressure graph 600 showing intraocular pressure variations with time in graphical form.

When a predetermined trigger signal is output, the control section 70 causes the probe 10 to continuously emit the ultrasonic wave pulse to the eye E at predetermined time intervals (e.g., 0.1 seconds intervals) and detect a reflected wave of the emitted ultrasonic wave pulse. An output signal from the probe 10 is then stored in the memory 75. In this way, waveform data of the reflected wave is obtained. In the case where a predetermined measurement condition is satisfied or a set measurement time has elapsed, the control section 70 stops the probe 10 from emitting the ultrasonic wave pulse. In this case, the measurement may be stopped based on a predetermined trigger signal.

When the waveform data of the reflected wave is stored in the memory 75, the control section 70 retrieves waveform data needed for the waveform indication 400 and displays the retrieved waveform data as the waveform indication 400. Specifically, the memory 75 stores many waveform data at each predetermined time interval, but all the waveform data do not always have to be used for the waveform indication 400. In this case, for example, the waveform data obtained in real time may be displayed on the monitor 72 at each step of certain time intervals or average data of the waveform data may be displayed on the monitor 72. The examiner checks in real time whether or not the reflected wave is detected properly based on the waveform indication 400 displayed on the monitor 72.

In this case, the waveform data of the reflected wave used in a calculation of the intraocular pressure value displayed in the intraocular pressure indication 500 (the details will be mentioned later) may be displayed on the monitor 72. For instance, the waveform data corresponding to each intraocular pressure value in the intraocular pressure value indication 500 may be displayed or an average of the waveform data corresponding to each intraocular pressure value may be displayed. Such display allows the examiner to check whether or not the reflected wave used in the intraocular pressure measurement was proper.

The control section 70 stores the output signal from the probe 10 in the memory 75 and then calculates an intraocular pressure value corresponding to the reflected wave of the emitted ultrasonic wave pulse. The control section 70 stores the obtained intraocular pressure value in association with measurement timing. Thus, the intraocular pressure of the eye E is continuously measured to obtain intraocular pressure variations with time.

The control section 70 obtains a predetermined number of intraocular pressure values by use of a predetermined reference based on the intraocular pressure values stored in the memory 75 and displays the obtained intraocular pressure values as the intraocular pressure value indication 500. In this case, for example, the control section 70 retrieves a maximum value Max, a medium value Med, and a minimum value Min from the obtained intraocular pressure values and displays them on the monitor 72. Furthermore, the control section 70 may display an average of the measurement values on the monitor 72. When a predetermined measurement value is to be obtained based on a distribution of the intraocular pressure values obtained as above, various kinds of statistical procedures may be used. A reference set to retrieve the intraocular pressure value data to be displayed as the intraocular pressure value indication 500 may be selected arbitrarily by the examiner.

The control section 70 creates the intraocular pressure graph 600 showing the variation with time of the intraocular pressure of the eye E by use of the intraocular pressure value stored in the memory 75 at each measurement time and displays the intraocular pressure graph 600 on the monitor 72. The intraocular pressure graph 600 is a graph taking a time on a lateral axis and an intraocular pressure value on a vertical axis, in which the intraocular pressure values obtained at the predetermined time intervals are indicated in association with the measurement timings. This display allows the examiner to visually recognize the variations in the intraocular pressure values due to pulsation. The intraocular pressure graph 600 may be shown in various display styles; for example, in a graph plotting intraocular pressure values at measurement timings or a graph plotting an approximated curve obtained by calculation based on each intraocular pressure value.

Furthermore, the control section 70 displays, on the intraocular pressure graph 600, indices 610 indicating the measurement timings of the measurement values displayed in the intraocular pressure value indication 500. In FIG. 10, on the waveform of the intraocular pressure graph 600, the indices 610 are marked at points corresponding to the maximum value, the medium value, and the minimum value in the intraocular pressure value indication 500. Such display allows the examiner to easily recognize a correspondence relation between the measurement values displayed in the intraocular pressure value indication 500 and the intraocular pressure graph 600. It is to be noted that the indices 610 may be displayed in various styles, for example, letters, figures, or a combination thereof.

The control section 70 displays a cycle information 620 showing a variation cycle of the intraocular pressure values due to pulsation on the intraocular pressure graph 600 in addition to the display of the indices 610. In this case, the control section 70 calculates the variation cycle based on the intraocular pressure values stored in association with the measurement times.

For the intraocular pressure graph 600, it is only necessary to set at least one of a first display mode of sequentially calculating the intraocular pressure value based on the output signal from the probe 10, sequentially updating the intraocular pressure graph, thereby displaying the intraocular pressure variation in real time and a second display mode of fixedly displaying the intraocular pressure graph showing the intraocular pressure values obtained in a predetermined time domain based on the output signal from the probe 10. In this case, the control section 70 may perform the control for the first display mode at an initial stage of measurement and, upon receipt of a predetermined trigger signal (e.g., when a freeze button provided on the operation section 74 is pressed), switch to the control for the second display mode. Furthermore, the first and second display modes may be selected either one during parameter setting.

Similarly, for the waveform indication 400, it is only necessary to set at least one of a mode of sequentially updating the waveform indication 400 based on the output signal from the probe 10 and a mode of fixedly displaying the waveform indication 400 showing the waveform obtained in the predetermined time domain based on the output signal from the probe 10.

The above configuration may be arranged to allow the examiner to select whether or not the waveform indication 400 and the intraocular pressure graph 600 are displayed on the monitor 72. As to the waveform indication 400, live waveform data of the reflected wave detected by the probe 10 may be output or waveform data processed by a predetermined window function may be output. A plurality of window functions may be prepared to selectively display waveform data by an arbitral window function.

In the case where the intraocular pressure is continuously measured several times as above, it is preferable to set emission intervals (measurement intervals) and emission time (measurement time) of the ultrasonic wave pulse to obtain the intraocular pressure value distribution showing variations in measurement values due to pulsation of the examinee. In this case, it is more preferable to set the emission intervals and emission time of the ultrasonic wave pulse in order to obtain at least the maximum value (peak), the minimum value (bottom), and the medium value of the intraocular pressure values. The emission intervals and emission time of the ultrasonic wave pulse may be set arbitrarily by the examiner on a predetermined parameter setting screen.

The control section 70 may be adapted to perform intraocular pressure measurement by detecting the pulsation cycle of the eye E based on the output signal from the probe 10 and continuously emitting the ultrasonic wave pulse in sync with the detected pulsation cycle. Thus, measurement timings corresponding to the pulsation of the eye E are determined.

Specifically, the control section 70 detects the timings at which the maximum value, the minimum value, and the medium value of the intraocular pressure values based on the output signal from the probe 10 and continuously emits the ultrasonic wave pulse in sync with the detected timings to perform the intraocular pressure measurement. This makes it possible to reduce a burden on the eye E. It may be adapted to detect the timing at which a predetermined intraocular pressure value (e.g., the medium value) is obtained and continuously emit the ultrasonic wave pulse in sync with the detected timing to perform the intraocular pressure measurement.

In the above explanation, the maximum value, minimum value, and medium value of the intraocular pressure values are obtained. Instead thereof, a measurement value exceeding a predetermined measurement value range (e.g., 4 mmHg from the medium value) with reference to a predetermined measurement value may be obtained. Furthermore, another alternative is to arbitrarily set the measurement value range.

To retrieve the intraocular pressure value to be output as the intraocular pressure value indication 500, the control section 70 may retrieve the intraocular pressure value obtained at each predetermined time interval (e.g., 0.3 second). The time intervals may be set arbitrarily by the examiner on the predetermined parameter setting screen.

In the above configuration, when continuous measurement is to be performed, a single intraocular pressure value may be obtained by use of a reflected wave by a single ultrasonic wave pulse or a single intraocular pressure value may be obtained by plural ultrasonic wave pulses.

The invention claimed is:

1. A non-contact ultrasonic tonometer for measuring intraocular pressure of an examinee's eye in non-contact manner by use of an ultrasonic wave, the tonometer comprising:
   a probe including a vibrator for making an ultrasonic pulse incident on a cornea of the eye and a sensor for detecting the ultrasonic pulse reflected from the cornea of the eye;
   a trigger signal generation unit which generates a trigger signal to start measurement; and
   a control unit which controls the probe to emit the ultrasonic pulse based on generation of the trigger signal at predetermined time intervals or a predetermined number of times within at least one pulsation cycle of the eye, and obtains an intraocular pressure value corresponding to a reflection wave characteristic of each ultrasonic pulse detected by the sensor based on an output signal from the probe.

2. The tonometer according to claim 1, wherein
the control unit detects a pulsation cycle of the eye based on the output signal from the probe and continuously emits the ultrasonic pulse in sync with the detected pulsation cycle.

3. The tonometer according to claim 1 further comprising:
a memory; and
a monitor,
wherein the control unit obtains intraocular pressure corresponding to a reflected wave of an ultrasonic pulse based on the output signal from the probe, stores a value of the obtained intraocular pressure in the memory in association with measurement timing, and displays, on the monitor, an intraocular pressure graph showing variations with time in the intraocular pressure based on the stored data and the intraocular pressure value.

4. The tonometer according to claim 3, wherein
the control unit displays a waveform of the reflected wave on the monitor based on the output signal from the probe.

5. The tonometer according to claim 3, wherein
the control unit displays, on the intraocular pressure graph, an index showing the measurement timing of the intraocular pressure value displayed on the monitor.

6. A non-contact ultrasonic tonometer for measuring intraocular pressure of an examinee's eye in non-contact manner by use of an ultrasonic wave, the tonometer comprising:
a probe including a vibrator for making an ultrasonic pulse incident onto the eye and a sensor for detecting the ultrasonic pulse reflected from the eye;
an alignment mark projection optical system which projects an alignment mark onto the eye;
an alignment mark detection optical system which detects the alignment mark projected onto the eye; and
a control section which determines whether an alignment state of the probe is proper or not with respect to the eye based on a detection result of the alignment mark, generates a trigger signal to start measurement based on a determination result that an alignment state of the probe is proper, controls the probe to emit the ultrasonic pulse based on generation of the trigger signal at predetermined time intervals or a predetermined number of times within at least one pulsation cycle of the eye, and obtains an intraocular pressure value corresponding to a reflection wave characteristic of each ultrasonic pulse detected by the sensor based on an output signal from the probe.

7. The tonometer according to claim 6, wherein
the control section detects a pulsation cycle of the eye based on the output signal from the probe and continuously emits the ultrasonic pulse in sync with the detected pulsation cycle.

8. The tonometer according to claim 6 further comprising:
a memory; and
a monitor,
wherein the control section obtains intraocular pressure corresponding to a reflected wave of an ultrasonic pulse based the output signal from the probe, stores a value of the obtained intraocular pressure in the memory in association with measurement timing, and displays, on the monitor, an intraocular pressure graph showing variations with time in the intraocular pressure based on the stored data and the intraocular pressure value.

9. The tonometer according to claim 1 further comprising:
a detection unit which detects an alignment state of the probe with respect to the eye;
a determination unit which determines whether the alignment state is proper or not based on a detection result of the detection unit; and
the trigger signal generation unit generates a trigger signal to start measurement based on a determination result of the determination unit that an alignment state of the probe is proper.

* * * * *